US008586103B2

United States Patent
Li et al.

(10) Patent No.: US 8,586,103 B2
(45) Date of Patent: Nov. 19, 2013

(54) NON-POLYMERIC COMPOSITIONS FOR CONTROLLED DRUG DELIVERY

(75) Inventors: Yuhua Li, Newark, DE (US); Andrew Guarino, Newark, DE (US); Benjamin Chien, Woodside, CA (US)

(73) Assignee: Foresee Pharmaceuticals, LLC, Newark, DE (US)

( * ) Notice: Subject to any disclaimer, the term of this patent is extended or adjusted under 35 U.S.C. 154(b) by 775 days.

(21) Appl. No.: 12/366,402

(22) Filed: Feb. 5, 2009

(65) Prior Publication Data

US 2010/0034801 A1  Feb. 11, 2010

Related U.S. Application Data

(60) Provisional application No. 61/065,178, filed on Feb. 8, 2008.

(51) Int. Cl.
*A01N 65/00* (2009.01)
(52) U.S. Cl.
USPC ....................................................... 424/725
(58) Field of Classification Search
None
See application file for complete search history.

(56) References Cited

U.S. PATENT DOCUMENTS

| 3,932,610 | A * | 1/1976 | Rudy et al. ............. 510/119 |
| 2002/0001631 | A1 | 1/2002 | Okumu |
| 2002/0132007 | A1 | 9/2002 | Randolph et al. |
| 2006/0210599 | A1 | 9/2006 | Gibson et al. |
| 2006/0228414 | A1 | 10/2006 | Cook |

FOREIGN PATENT DOCUMENTS

JP    10218745    *  8/1998

OTHER PUBLICATIONS

Galina N. Rudenskaya, et al, BMC Structural Biology vol. 4:2 (2004).

* cited by examiner

*Primary Examiner* — Michael Meller
(74) *Attorney, Agent, or Firm* — VLP Law Group LLP (57) ABSTRACT

The present invention provides a novel liquid composition suitable for in-situ formation of a depot system to deliver a bioactive substance in a controlled manner. The composition of the present invention comprises: (a) a hydrophobic non-polymeric carrier material; (b) a water miscible biocompatible organic solvent that dissolves the hydrophobic non-polymeric material; (c) an ionic complex that is formed between an amphiphilic molecule and a bioactive substance having a net charge at neutral pH in water. The present invention also provides a method of manufacturing and use of the composition thereof.

11 Claims, 2 Drawing Sheets

Figure 1. Pictures taken after the formulations stood at room temperature for 1 h (a) and 24 h (b).

Figure 2. *In vitro* release of octreotide from SAIB/NMP formulations containing (a) OCT-Ac; (b) OCT-SDS; (c) OCT-DSS Figure 3. *In vitro* release of leuprolide from SAIB/NMP formulations containing (a) LA-Ac; (b) LA-SDS; (c) LA-DSS; (d) LA-OL Figure 4. *In vitro* release of pramipexole from SAIB/NMP formulations containing (a) PPL-HCl and (b) PPL-SDS.

NON-POLYMERIC COMPOSITIONS FOR CONTROLLED DRUG DELIVERY

FIELD OF THE INVENTION

This invention relates to the field of controlled release delivery of bioactive substances and to compositions and methods useful for controlled release delivery of bioactive substances using a hydrophobic, non-polymeric material as a carrier.

BACKGROUND OF THE INVENTION

Hydrophobic, non-polymeric materials, particularly, highly viscous, non-polymeric liquid materials have been described as biodegradable systems for controlled release delivery of bioactive compounds (Smith and Tipton, *Pharmaceutical Research,* 13(9), S300, 1996). The hydrophobic non-polymeric material is generally substantially insoluble in water. The hydrophobic non-polymeric material can be a highly viscous liquid that has a viscosity of at least 5,000 cP at 37° C. and does not crystallize neat under ambient or physiological conditions. When such material is mixed with a small amount of plasticizing solvent, the mixture has much lower viscosity than that of the non-polymeric liquid material alone. This low viscosity solution can be easily formulated with a bioactive compound and the resulting low viscosity liquid formulation can be readily administered to a subject to form a highly viscous depot in-situ.

Representative examples of such in-situ forming depot systems containing the hydrophobic, non-polymeric liquid carrier materials are disclosed in the U.S. Pat. Nos. 5,747,058; 5,968,542; 6,051,558; and 6,992,065. The compositions described in these patents comprise a hydrophobic, highly viscous, non-polymeric liquid material such as sucrose acetate isobutyrate (SAIB), a water soluble or miscible organic solvent, and a bioactive substance. Such a composition can be easily prepared and administered to a subject in the form of a low viscosity solution. Once in the body, the solvent dissipates or diffuses into the surrounding tissues, which leads to the precipitation or coagulation of the non-polymeric materials to form a highly viscous gel, semi-solid, or solid depot that encapsulates the bioactive substances. Then the bioactive substance is released via dissolution, diffusion, and/or degradation of the depot.

The non-polymeric carrier materials are typically degraded through the hydrolysis of the ester or ester-like bond. The cleavage of esters is facilitated nucleophilic groups, such as amine groups, within an enzyme or other bioactive substances. This facile degradability is advantageous for medical use, but the susceptibility of the formulation to degradation also presents a major problem for preparing stable formulations. Whenever a bioactive substance is combined with the non-polymeric liquid carrier materials, that same degradation can occur through the interaction between the bioactive substances and the non-polymeric carrier material. Such an interaction can adversely affect the physical and chemical characteristics of the composition resulting in undesired degradation of non-polymeric material and generation of impurities of the bioactive substance. The instability of the carrier material and the bioactive substance in the formulation will prevent the preparation of a suitable composition for storage with a reasonable shelf-life and for use of the formulation to form a consistent depot upon administration with desired release characteristics.

In addition, due to the hydrophobic nature of the non-polymeric carrier material, many bioactive agents, especially hydrophilic peptides and proteins with their charged and polar characteristics, may not be compatible with the non-polymeric carrier material, resulting in an unstable liquid formulation. Phase separation has been commonly observed when hydrophobic non-polymeric carrier materials are combined with an uncomplexed bioactive substance or its simple salt, such as acetate or hydrochloride salt. The phase separation during formulation, storage and in situ depot formation results in a non-homogeneous formulation or depot that leads to uncontrolled release characteristics. In addition, an initial burst release is the typical characteristic of this type of liquid formulations as evidenced in the prior art U.S. Pat. Nos. 5,747,058 and 5,968,542. The uncontrollable initial burst may not be desirable, especially for bioactive substances with a narrow therapeutic index.

Therefore, there is a need to develop a controlled release composition that will prevent or minimize undesirable interactions between the non-polymeric carrier materials and bioactive substances. There is also a need to develop a controlled release composition that can be formulated and stored as a single-phase homogeneous composition of non-polymeric carrier material and bioactive substance. There is a further need to develop such a single-phase homogeneous composition that will provide a depot with a low initial burst release.

SUMMARY OF THE INVENTION

The present invention provides a novel liquid composition suitable for in-situ formation of a depot system to deliver a bioactive substance in a controlled manner. The composition of the present invention comprises: (a) a hydrophobic non-polymeric carrier material; (b) a water miscible biocompatible organic solvent that dissolves the hydrophobic non-polymeric material and lowers the viscosity of the composition significantly to facilitate the ease of preparation and administration; (c) an ionic complex that is formed between an amphiphilic molecule and a bioactive substance having a net charge at neutral pH in water. Wherein the non-polymeric material is substantially insoluble in water and may be a highly viscous liquid that has a viscosity of at least 5,000 cP at 37° C. and does not crystallize neat under ambient or physiological conditions The composition of the present invention may further comprise an additive to achieve desired release characteristics. The present invention also provides a method of manufacturing and use of the composition thereof.

Accordingly, a bioactive substance is preferably combined with an amphiphilic molecule to form an ionic complex that is substantially insoluble in water or biological fluid. Then the ionic complex of the bioactive substance is dispersed in the solution of the hydrophobic non-polymeric carrier material in a water-miscible solvent such as N-methyl-2-pyrrolidone (NMP) to form a homogeneous solution or uniform suspension. Typically, when an uncomplexed bioactive substance or its simple salt, such as acetate or hydrochloride salt, is combined with a hydrophobic non-polymeric material in an organic solvent, phase separation occurs. However, it has been unexpectedly discovered that the use of the ionic complex of bioactive substance with amphiphilic molecule of the present invention can prevent or minimize the phase separation to maintain the physical stability of the formulation. In addition, the uncomplexed bioactive substance or its simple salt, such as acetate or hydrochloride salt, is susceptible to chemical degradation during formulation process and subsequent storage. Such chemical degradation can be prevented or minimized by complexing the bioactive substance with amphiphilic molecules of the present invention. The enhanced chemical and physical stabilities of the composition will allow the development of a stable product with a desired release characteristics and a reasonable storage shelf life.

When the non-polymeric liquid composition of the present invention is brought in contact with an aqueous environment, such as biological fluids in the body of a subject, the water soluble or miscible solvent dissipates or diffuses into the surrounding aqueous or biological fluids. Simultaneously, the hydrophobic non-polymeric liquid carrier material precipitates or coagulates to form a highly viscous gel or solid depot that traps or encapsulates the bioactive substance. Due to the rapid diffusion of the solvent, typically a high initial burst release of the bioactive substance is observed during the depot formation process. However, it has been unexpectedly found that the complexation of bioactive substances with suitable amphiphilic molecules of the present invention dramatically reduces the burst effect and improves the overall release profile of the bioactive substance relative to the formulation containing uncomplexed bioactive substance or its simple salt such as acetate salt. Once the depot is formed, the bioactive substance is released from the non-polymeric matrix by dissolution, diffusion and/or degradation of the non-polymeric carrier material.

According to the present invention, the composition optionally includes additives that modify the composition to achieve desired release profile for the bioactive substance. The additives include, but are not limited to, burst effect reducing materials, release rate retarding agents, release rate accelerating agents, solubilization agents and the like. The additives can be polymeric or non-polymeric materials including biodegradable or non-biodegradable polymers, carbohydrates or carbohydrate derivatives, organic or inorganic compounds.

The composition of the present invention may be a viscous or non-viscous liquid, or gel that may be easily injected using a syringe or similar device. The composition can be administered by injection subcutaneously, intramuscularly, intraperitoneally, or intradermally to form a depot in-situ. The compositions can also be administered orally or topically or transmucosally. When administered to the body of a subject, the controlled release of the bioactive substance can be controlled for a desired period of time depending upon the composition of the system. With the proper selections of the non-polymeric carrier material and other excipients, the duration of the controlled release of the bioactive substance can be controlled over a period of time from several weeks to one year.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

The present invention provides a non-polymeric liquid composition suitable for in-situ formation of a depot system to deliver bioactive substances in a sustained and controlled manner. The preferred non-polymeric liquid composition of the present invention is a combination of at least a hydrophobic non-polymeric carrier material, a bioactive substance, an amphiphilic molecule, and a water-soluble or miscible biocompatible solvent. Preferably, the bioactive substance is associated with the amphiphilic molecule in the form of an ionic complex that is substantially insoluble in water. Optionally, additives can be included to modify the composition to achieve desired release characteristics. The composition is in the liquid form that may be viscous or non-viscous. The composition is a homogeneous solution or uniform suspension. All the components of the present invention are biocompatible and stable during formulation process and storage under suitable conditions.

The composition of the present invention is preferably injectable using a syringe or any other similar devices. The composition can be administered to the body of a subject by injection subcutaneously, intramuscularly, intraperitoneally, or intradermally to form a depot in-situ. The compositions can also be administered orally or topically or transmucosally. When administered to the body of a subject, upon contact with an aqueous environment or body fluid, the solvent dissipates or diffuses into the surrounding fluid and the hydrophobic, non-polymeric carrier material precipitates or coagulates to form a viscous gel, semi-solid or solid depot. The depot may be porous or non-porous. The incorporated bioactive substance is substantially encapsulated in the depot and is released gradually over time. Preferably, the composition of the present invention has an initial release less than 20% within 24 hours, more preferably less than 10% within 24 hours, most preferably less than 5% within 24 hours. With the proper selections of the non-polymeric carrier material and other components of the composition, the duration of the controlled release of the bioactive substance can be controlled over a period of time from several weeks to one year.

As used herein, the terms "a", "an" and "one" are meant to be interpreted as "one or more" and "at least one", unless the content clearly dictates otherwise.

The carrier material is any hydrophobic, non-polymeric material that is biodegradable, biocompatible, and substantially insoluble in water and biological fluid. The hydrophobic non-polymeric carrier material is preferably a highly viscous liquid having a viscosity of at least 5,000 cP at 37° C. that does not crystallize neat under ambient or physiological conditions. The term "hydrophobic" refers to the physical property of a molecule that tends not to dissolve in or mix with or be wetted by water. Specifically as used herein, it refers to the solubility of a material in water is less than one percent by weight at 25° C. The term "non-polymeric" refers to esters or mixed esters having essentially no repeating units in the acid moiety of the esters. Some examples, without limitation, of the hydrophobic, non-polymeric liquid carrier materials are described in the prior art U.S. Pat. Nos. 5,747,058; and 5,968,542, which are incorporated herein entirely by reference.

Particularly, the hydrophobic non-polymeric carrier materials can be one or more of non-polymeric esters or mixed esters. The esters are typically formed from a polyol having less than 20 hydroxyl groups that are esterified with carboxylic acids. Suitable polyols include monofunctional and multifunctional alcohols having from 2 to 24 carbons, sugar alcohols, monosasaccharides, disacchrides, oligosacchrides, and polyether alcohols. More specifically, the polyols may be dodecanol, hexanediol, glycerol, mannitol, sorbitol, glucose, fructose, sucrose, inositol, polyglycerol, polyethylene glycol, and the like.

The carboxylic acids used to form the hydrophobic non-polymeric carrier materials include organic acids having more than two carbons, such as fatty acids. These carboxylic acids may be saturated, unsaturated, aromatic (aryl or arylalkyl) and linear or branched in structure. These carboxylic acids may also have one or more hydroxyl groups or other groups such as halo, nitro and the like. More specifically, these carboxylic acids include acetic acid, propionic acid, butyric acid, isobutyric acid, valeric acid, lipoic acid, hexanoic acid, heptanoic acid, oleic acid, palmitic acid, stearic acid, myristic acid, benzoic acid, glycolic acid, lactic acid, ε-hydroxycaproic acid, octanoic acid, decanoic acid, dodecanoic acid, tetradecanoic acid, hexadecanoic acid, octadecanoic acid, eicosanoic acid, docosanoic acid, and other fatty acids.

The hydrophobic non-polymeric carrier material is preferably biodegradable without the generation of any non-biocompatible or toxic degradants. When the hydrophobic non-polymeric carrier material is mixed with a water miscible solvent, a solution of low viscosity can be obtained. The low viscosity solution can be readily combined with a bioactive substance to prepare the composition of the present invention. The low viscosity allows the composition to be easily administered to the body of a subject. The characteristics of the composition will vary according to the factors such as the miscibility of the non-polymeric material in the solvent, the concentration of the non-polymeric material in the formulation, the concentration of the bioactive substances, and/or the presence of additives. These parameters of the composition can be adjusted to obtain desired characteristics.

In a preferred embodiment, sucrose acetate isobutyrate (SAIB) is used as a hydrophobic non-polymeric carrier material. The SAIB is a mixed ester of sucrose esterified with two acetate and six isobutyrate groups. The ester is completely non-crystalline and has a viscosity of over 100,000 cP at 30° C. The viscosity of the ester can be dramatically decreased by slightly increasing the temperature or adding solvents. In one embodiment, the SAIB is heated and mixed with a bioactive substance to prepare a suspension. Alternatively, the SAIB can be mixed with a large number of different biocompatible solvents to result in a low viscosity solution that can be easily formulated with a bioactive substance.

Suitable solvents for optional use in the composition of the present invention are biocompatible and water soluble or miscible to dispersible. As used herein, the terms "soluble" and "miscible" are equivalent and can be used interchangeably and refer to the solubility of the solvents in water at 25° C. is at least 1%, preferably at least 3%, more preferably at least 7% by weight. When combined with the hydrophobic non-polymeric carrier material, the solvents can dramatically reduce the viscosity of the mixture to form a lower viscosity liquid carrier material. Such lower viscosity liquid composition can be further formulated with a bioactive substance for controlled release delivery. Examples of the suitable solvents, without limitation, include acetone, benzyl alcohol, butylene glycol, caprolactam, caprolactone, dimethylsulfoxide (DMSO), ethanol, ethyl acetate, ethyl lactate, glycerol, glycerol formal, glycofurol(tetraglycol), N-methyl-2-pyrrolidone (NMP), polyethylene glycol, methoxy polyethylene glycol, alkoxy polyethylene glycol, propylene carbonate, 2-pyrrolidone, triacetin, triethyl citrate, and combinations thereof.

As used herein, the term "bioactive substance" is meant to include any materials having diagnostic and/or therapeutic properties including, but are not limited to, small molecules, macromolecules, peptides, proteins, or enzymes. Non-limiting examples of therapeutic properties are antimetabolic, antifungal, anti-inflammatory, anti hypertensive, anti psychotic, analgesic, antidiabetic, hypnotic, sedating, anesthetic, antitumoral, antiinfectious, antibiotic, antiviral, hormonal, nutrient, agonist, and antagonist properties.

More specifically, suitable bioactive substances of the present invention include any compounds that are ionizable, have a net charge at neutral pH in water and can form an ionic complex with an amphiphilic molecule. Preferably such a compound contains an electron donor base group such as a basic nitrogen atom, e.g. an amine, imine or ring nitrogen. The bioactive substances of the present invention include, but are not limited to, doxorubicin, 4-hydroxy-phenethylamine, methylamphetamine, amitriptyline, reboxetine, bupropion, mirtazapine, venlafaxine, duloxetine, fluoxetine, paroxetine, escitalopram, citalopram, sertraline, bromocriptine, pergolide, pramipexole, ropinirole, cabergoline, apomorphine, lisuride, doxycyclin, diltiazam, cyclobenzaprine, bacitracin, noscapine, erythromycin, polymyxin, vancomycin, nortriptyline, quinidine, ergotamine, benztropine, verapamil, flunarizine, imipramine, kanamycin, neomycin, amoxicillin, amikacin, arbekacin, bambermycins, butirosin, dibekacin, dihydrostreptomycin, fortimicin, isepamicin, micronimicin, netilmicin, paromycin, ribostamycin, rapamycin, sisomicin, streptomycin and tobramycin, streptomycin and tobramycin, pyrimethamine, naltrexone, lidocaine, prilocalne, mepivacaine, bupivacaine, tetracaine, ropivacaine, haloperidone and resperidone.

The bioactive substances of the present invention further include oxytocin, vasopressin, adrenocorticotropic hormone (ACTH), epidermal growth factor (EGF), platelet-derived growth factor (PDGF), prolactin, luteinising hormone, luteinizing hormone releasing hormone (LHRH), LHRH agonists, LHRH antagonists, growth hormones (including human, porcine, and bovine), growth hormone releasing factor, insulin, erythropoietin (including all proteins with erythropoietic activity), somatostatin, glucagon, interleukin, interferon-α, interferon-β, interferon-γ, gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), exenatide, peptide YY (PYY), renin, bradykinin, bacitracins, polymyxins, colistins, tyrocidine, gramicidins, cyclosporins (which includes synthetic analogues and pharmacologically active fragments thereof), enzymes, cytokines, antibodies, vaccines, antibiotics, antibodies, glycoproteins, follicle stimulating hormone, kyotorphin, taftsin, thymopoietin, thymosin, thymostimulin, thymic humoral factor, serum thymic factor, colony stimulating factors, motilin, bombesin, dinorphin, neurotensin, cerulein, urokinase, kallikrein, substance P analogues and antagonists, angiotensin II, blood coagulation factor VII and IX, lysozyme, gramicidines, melanocyte stimulating hormone, thyroid hormone releasing hormone, thyroid stimulating hormone, pancreozymin, cholecystokinin, human placental lactogen, human chorionic gonadotrophin, protein synthesis stimulating peptide, gastric inhibitory peptide, vasoactive intestinal peptide, platelet derived growth factor, and synthetic analogues and modifications and pharmacologically-active fragments thereof.

In accordance with the present invention, the bioactive substance is complexed with an amphiphilic molecule through an ionic interaction. The association with the amphiphilic molecule stabilizes the bioactive substance in the composition of the present invention. The combination of the complex with the other formulation components produces a delivery system that has practically sufficient stability to provide a physically consistent and controllable delivery system. More specifically, the amphiphilic molecule serves to prevent or minimize the chemical degradation of the bioactive substance, to maintain the physico-chemical stability of the composition of the present invention, and to reduce the initial burst release of the bioactive substance from the depot formed from the composition. Such a system can be used to consistently treat patients with various diseases.

Suitable amphiphilic molecules of the present invention is any material having a hydrophobic portion and a hydrophilic portion. The hydrophilic portion of the amphiphilic molecule is ionic, and preferably anionic. The amphiphilic molecule may be an organic sulfuric acid, organic sulfonic acid, organic phosphoric acid, or organic carboxylic acid. Particularly, organic sulfuric acid and organic sulfonic acid are preferred. The amphiphilic molecule may also be in different salt or ionic (dissociated) forms of the molecule. The hydrophobic portion of the amphiphilic molecule may be any hydrophobic group such as alkyl, aryl, or arylalkyl groups. The hydrophobic portion may be saturated, unsaturated, aromatic (aryl or arylalkyl) and linear or branched in structure. The hydrophobic portion is preferably an alkyl or substituted alkyl group of at least 4 carbons. The amphiphilic molecule associates with the bioactive substance to form an ionic complex that is substantially insoluble in water under ambient condition. The term "substantially insoluble" refers to the complex having a solubility of less than 5%, preferably less than 1% by weight under ambient conditions.

Some specific examples of the amphiphilic molecules of the present invention include, but are not limited to, mono-C12-18-alkyl sulfate sodium salts, dialkyl ester sulfosuccinic acid derivatives having 3 to 16 carbon atoms, dioctyl sulfosuccinic acid, benzenesulfonic acid, naphthalene-1,5-disulfonic acid, camphorsulfonic acid, (+)-(1S)-camphor-10-sulfonic acid, dodecylsulfuric acid, para-toluenesulfonic acid, naphthalene-2-sulfonic acid, cholesterol sulfate, heptanesulfonic acid, capric acid, caproic acid, caprylic acid, cinnamic acid, oleic acid, palmitic acid, pamoic acid, benzoic acid, stearic acid, undecylenic acid, and phospholipids. These examples also include different salt and/or ionic (dissociated) forms of the molecules.

According to the present invention, the composition optionally includes additives that modify the composition to achieve desired release profile for the bioactive substance. The additives may be included to modulate release rate and stabilize the bioactive substance. Suitable additives can be any polymeric or non-polymeric materials including biodegradable or non-biodegradable polymers, carbohydrates or carbohydrate derivatives, organic or inorganic compounds.

Some suitable additives are described in U.S. Pat. No. 5,747,058, which is incorporated herein entirely by reference. Preferably, the suitable additives are biocompatible and/or biodegradable polymers. Such polymers include, but are not limited to, polylactides, polyglycolides, polycaprolactones, polyanhydrides, polyamines, polyurethanes, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, chitin, chitosan, hyaluronic acid and copolymers, terpolymers and mixtures thereof.

According to the present invention, the composition optionally includes reducing agents, antioxidants, and free radical scavengers to stabilize the composition. Examples are, but are not limited to, cysteine or methionine, d-alpha tocopherol acetate, dl-alpha tocopherol, ascorbyl palmitate, butylated hydroxyanidole, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutyrophenone, dimethylphenol, ditertbutylphenol, vitamin E, and lecithin.

Accordingly, the composition of the present invention can be readily prepared. In one embodiment, the complex of a bioactive substance and an amphiphilic molecule may be prepared in any suitable manner. For example, a suitable amount of amphiphilic molecule that may or may not be in a solution form may be added to a suitable solution, such as an aqueous solution, of the bioactive substance to form the complex that is precipitated from the solution. The precipitate is then recovered using suitable means, such as centrifugation or filtration. In another embodiment, both bioactive substance and amphiphilic molecule are dissolved in water, and then the two solutions are combined. Upon contacting, the complexation between the bioactive substance and the amphiphilic molecule occurs and a precipitate is formed. In a further embodiment, both bioactive substance and amphiphilic molecule are dissolved in an organic solvent, and then the complex is recovered by removing side-product and evaporating off the solvent.

The ratio of the bioactive substance to the amphiphilic molecule in the complex is preferably about 0.1:1 to about 10:1 expressed on a molar basis. More preferably, the ratio is at stoichiometry based on the number of charged functional groups on both the bioactive substance and the amphiphilic molecule. In order to achieve optimal complexation and subsequent formulation, the molecular weight of the bioactive substance divided by the number of ionizable (charged) groups of the bioactive substance is preferably greater than 100 daltons. The resulting complex between the bioactive substance and the amphiphilic molecule is preferably substantially insoluble in water. Such a complex may be combined with the hydrophobic non-polymeric carrier materials, the solvent and other optional additives to form a uniform formulation. It has been surprisingly discovered that the association of the amphiphilic molecule with a bioactive substance prevents or minimizes the chemical degradation of the bioactive substance, maintains the physico-chemical stability of the composition of the present invention, and reduces the initial burst release of the bioactive substance from the composition. Therefore, the composition of the present invention is suitable for storage with a reasonable shelf life under suitable conditions.

As used herein, the term "ionizable group" refers to an atom or a group of atoms that can gain a net electric charge by adding or removing one or more electrons.

According to the present invention, the composition preferably is a uniform solution or homogeneous suspension. The maintenance of the uniformity or homogeneity of the composition is critical to allow reproducible administration and obtain consistent depot system for controlled release delivery of bioactive substances. Practically, the uniformity or homogeneity of the composition can be obtained at least by reconstitution or mixing immediately prior to administration. Preferably, the uniformity or homogeneity of the composition can be consistently maintained throughout the preparation process, storage and administration.

According to the present invention, the composition contains from about 99.5% to about 5% of the hydrophobic non-polymeric carrier material, preferably between 95% and 25% by weight relative to the total weight of the composition. The composition also includes about 0% to about 50% of a biocompatible solvent, about 0.1% to about 40% of a bioactive substance and sufficient amount of amphiphilic molecule to stabilize the formulation and the bioactive substance. The composition further contains about 1% to about 25% of one or more additives.

In one embodiment, a bioactive substance is first combined with an amphiphilic molecule to form a water substantially insoluble complex. This complex is then combined with the remaining components of the composition of the present invention to form a complete delivery system for packaging and storage. Preferably the composition is packaged in syringes in a ready-to-use configuration. Alternatively, this complex may be combined with the remaining components of the present invention immediately prior to administration to the body of a subject.

In a preferred embodiment, sucrose acetate isobutyrate (SAIB) is used as the hydrophobic non-polymeric carrier material and NMP is selected as the solvent. The bioactive substance is selected from a group consisting of peptides and proteins, such as octreotide, leuprolide, or glyeagon like peptide-1 (GLP-1). The bioactive substance is preferably combined with an amphiphilic molecule, preferably dioctyl sulfosuccinic acid or dodecylsulfuric acid, to form a water substantially insoluble complex. The resulting complex can be combined with the SAIB/NMP solution to form a controlled delivery formulation.

In another embodiment, the release rate of the compositions of the present invention was determined in vitro. About 0.1 mL of each formulation was injected into 3 mL of releasing buffer (PBS 7.4, containing 0.1% sodium azide) in a 4 mL glass vial. The vials were incubated at 37° C. and sampled at various time points. At each time point, 2 mL of release medium was removed and replaced with 2 mL of fresh release medium. The collected samples were analyzed for bioactive substance concentration and integrity by HPLC using an YMC-Pack ODS-120A column or equivalent. Triplicate samples were used for each formulation.

According to the present invention, the composition described herein can be administered to a subject where controlled release delivery of a bioactive substance is desired. As used herein, the term "subject" is intended to include warm-blooded animals, preferably mammals, more preferably humans.

As used herein, the term "administered" is intended to refer to dispensing, delivering or applying a composition (e.g., pharmaceutical formulation) to a subject by any suitable route for delivery of the composition to the desired location in the subject. The composition can be administered to a subject topically, subcutaneously, intramuscularly, intraperitoneally, or intradermally, and by oral, rectal, vaginal, or nasal administration to provide the desired dosage of a bioactive substance based on the known parameters for treatment of the various diseases with the bioactive substances.

The term "controlled or controlled release delivery", as used herein, includes, for example, continual delivery of a bioactive substance in vivo over a period of time following administration, preferably at least several days to weeks or months. Controlled or controlled release delivery of the bioactive substance can be demonstrated, for example, by the continued therapeutic effect of the agent over time (e.g., for leuprolide, controlled delivery of the peptide can be demonstrated by continued testosterone suppression over time). Alternatively, controlled delivery of the agent may be demonstrated by detecting the presence of the agent in vivo over time.

In this application, the various embodiments set forth in the claims for the instant liquid non-polymeric compositions are also envisioned, mutatis mutandis, for the instant methods for forming such compositions and the instant methods for forming depots in situ.

EXAMPLES

The following examples illustrate the features and scope of the present invention. The following examples should not be considered as any limitations, but should be merely interpreted to teach how to make the useful drug delivery systems.

Example 1

Preparation of Formulation Containing Octreotide Acetate and In Vitro Release A solution of sucrose acetate isobutyrate (SAIB) in N-methyl-2-pyrrolidone (NMP) at a concentration of 80% by weight was prepared by combining 2 g NMP with 8 g SAIB followed by gentle mixing. A clear, low viscosity solution was obtained. Then 60 mg octreotide acetate was dissolved in 100 μL NMP which was combined with 900 μL SAIB solution in NMP (80%) and mixed well to obtain a formulation containing about 6% of octreotide acetate.

About 0.1 mL of the octreotide formulation was injected into 3 mL of releasing buffer (PBS 7.4, containing 0.1% sodium azide) in a glass vial. The vials were incubated at 37° C. and sampled at various time points. At each time point, 2 mL of release medium was removed and 2 mL of fresh release medium added. The release samples were analyzed for peptide concentration and integrity by HPLC using a YMC-Pack ODS-120A column.

Observation: when 100 μL solution of octreotide acetate in NMP was mixed with 900 μL SAIB solution in NMP (80%), an opaque suspension with chunky aggregates was surprisingly obtained. Since both SAIB and octreotide acetate were quite soluble in NMP, a clear solution was expected after two solutions in the same solvent (NMP) were mixed. This indicates that the octreotide or octreotide acetate is not very compatible with SAIB. When the suspension was allowed to stand at room temperature, the appearance of phase separation was observed within a few hours, and two distinguished phases were obtained after stood at room temperature overnight. Therefore, such a formulation is not suitable for preparation of a stable, single-phase formulation of octreotide in SAIB/NMP solution.

HPLC analysis of the formulation stored at room temperature for various periods of time unexpectedly showed several extra different peaks on the chromatogram. Those peaks were not observed from the formulation at the beginning, indicating the generation of impurities or degradation products of the octreotide. The intensity of these peaks increased with the increase of time, while the peak for octreotide decreases over time. This result suggested that the chemical instability of the bioactive substance and other excipients in the formulation would be an obstacle for successful development of a single-phase stable product. Therefore, this type of formulation must be modified to be suitable for controlled release delivery of various bioactive substances.

Example 2

Preparation of the Complex of Octreotide and Dodecyl Sulfate (OCT-SDS)

215.2 mg of sodium dodecyl sulfate (SDS, MW 288.38, 98.5%) was dissolved in 20 ml water (10.76 mg/mL, 36.75 mM). 251.7 mg (0.212 mmol) of octreotide acetate (MW 1019.2+120 (acetate), 85.8%) was dissolved in water (10 mL). The octreotide solution was mixed with 11.56 mL of the SDS solution to form the complex stoichiometrically. The precipitate was separated by centrifugation and then dried under vacuum.

Example 3

Preparation of the Complex of Leuprolide and Dodecyl Sulfate (LA-SDS)

215.2 mg of sodium dodecyl sulfate (SDS, MW 288.38, 98.5%) was dissolved in 20 mL water (10.76 mg/mL, 36.75 mM). 201.4 mg (0.142 mmol) of leuprolide acetate (MW 1209.4, 85.1%) was dissolved in 10 mL water (14 mM). The leuprolide solution was mixed with 7.619 mL of the SDS solution to form the complex stoichiometrically. The precipitate was separated by centrifugation and then dried under vacuum.

Example 4

Preparation of the Complex of Octreotide and Docusate (OCT-DSS)

1,4-Bis(2-ethyhexyl)sulfobutanedioate sodium or sodium docusate (DSS, $C_{20}H_{37}NaO_7S$, MW: 444.56, 506.6 mg, 1.139 mmol) was dissolved in isopropanol (20 mL) (56.97 mM), and 201.4 mg (0.17 mmol) of octreotide acetate (MW 1019.2, 85.8%) was dissolved in 10 mL water (17 mM). 5.968 mL of DSS solution was mixed with octreotide solution and stirred for about one hour. The complex was separated by centrifugation, and the resulting precipitate was washed with water and then dried under vacuum.

Example 5

Preparation of the Complex of Leuprolide and Docusate (LA-DSS)

1,4-Bis(2-ethyhexyl)sulfobutanedioate sodium (DSS, $C_{20}H_{37}NaO_7S$, MW: 444.56, 506.6 mg, 1.139 mmol) was dissolved in isopropanol (20 mL) (56.97 mM), and 250 mg (0.176 mmol) of leuprolide acetate (MW 1209.4, 85.1%) was dissolved in water (10 mL). 6.178 mL of the DSS solution was mixed with the leuprolide solution and stirred for one hour. The complex was separated by centrifugation, and the resulting precipitate was washed with water and then dried under vacuum.

Example 6

Preparation of Leuprolide Oleate (LA-OL)

77.4 mg of leuprolide acetate (MW 1209.4, 84.2%) was dissolved in 1 mL of DI water (0.0539 mmol). 31.38 mg of oleic acid (#A0241935, MW 282.46, 97%) was added to obtain a 1:2 molar ratio of LA:OL. A white precipitate formed upon mixing the solution. The complex was separated by centrifugation, and the resulting precipitate was washed with water and then dried under vacuum.

Example 7

Preparation and In Vitro Characterization of Formulations Containing Octreotide

Octreotide acetate (OCT-Ac), octreotide dodecyl sulfate (OCT-SDS) and octreotide docusate (OCT-DSS) complex powders were dissolved in NMP. Then the solutions containing various salt forms of octreotide were thoroughly mixed with SAIB solution in NMP (90% w/w). The octreotide content was about 6% for all formulations and the SAIB concentration was about 70% as shown in Table 1.

TABLE 1

Formulations containing octreotide

| Formulation | Peptides (mg) | SAIB (mg) | NMP (mg) | Peptide Content (%) |
|---|---|---|---|---|
| OCT-Ac/SAIB/NMP | 65.9 | 653.5 | 281.8 | 6% |
| OCT-SDS/SAIB/NMP | 88.5 | 629.5 | 280.1 | 6% |
| OCT-DSS/SAIB/NMP | 104.0 | 619.1 | 278.9 | 6% |

When the OCT-Ac was combined with SAIB/NMP solution, phase separation occurred immediately. Chunky solid precipitates were observed and an inhomogeneous formulation was obtained as observed in Example 1. This inhomogeneous formulation will block needles and is not suitable for injection. When the complex of octreotide with sodium dodecylsulfate (OCT-SDS) was combined with SAIB/NMP solution, a homogeneous suspension was obtained and suitable for injection. This formulation can be prepared immediately prior to administration or suitable for storage for a period of time by adjusting the formulation parameters. When the complex of octreotide with sodium docusate was combined with SAIB/NMP solution, a transparent uniform solution was obtained, and no phase separation occurred. This formulation may be packaged and stored for a long period of time at room temperature.

In addition, it was found that octreotide was not stable in the formulation containing OCT-Ac, which confirmed the finding in the Example 1 above. As shown in Table 2, the generation of the impurities of the octreotide occurred as soon as the components were combined. After two hours, about 4% of the octreotide was degraded or reacted. More than half of the octreotide was degraded after 5 days, indicating that the system is not suitable for the controlled delivery of the peptide. However, it was unexpectedly found that little or no degradation of the octreotide was detected from the formulations containing OCT-SDS and OCT-DSS even after seven days at room temperature (Table 2).

TABLE 2

The stability of the octreotide in formulations at room temperature over time

| Time (day) | OCT-Ac/SAIB/NMP | OCT-SDS/ SAIB/NMP | OCT-DSS/ SAIB/NMP |
|---|---|---|---|
| 0.08 | 96.1 | 99.4 | 100 |
| 1 | 90.8 | 99.3 | 99.5 |

TABLE 2-continued

The stability of the octreotide in formulations at room temperature over time

| Time (day) | OCT-Ac/SAIB/NMP | OCT-SDS/ SAIB/NMP | OCT-DSS/ SAIB/NMP |
|---|---|---|---|
| 2 | 71.9 | 100 | 100 |
| 5 | 48.7 | 100 | 99.8 |
| 7 | 41.4 | 100 | 98.9 |

Example 8

Preparation and In Vitro Characterization of Formulations Containing Octreotide

Octreotide acetate (OCT-Ac) and octreotide dodecyl sulfate (OCT-SDS) complex powders were dissolved in NMP. Then the solutions containing various salt forms of octreotide were thoroughly mixed with SAIB solution in NMP (90% w/w). The final octreotide content was about 6% for all formulations and the SAIB concentration was about 80% as shown in Table 3.

TABLE 3

Formulations containing octreotide

| Formulation | Peptides (mg) | SAIB (mg) | NMP (mg) | Peptide Content (%) |
|---|---|---|---|---|
| OCT-Ac/SAIB/NMP | 62.9 | 745.6 | 187.3 | 6% |
| OCT-SDS/SAIB/NMP | 61.4 | 467.3 | 130.8 | 6% |

Figure 1:
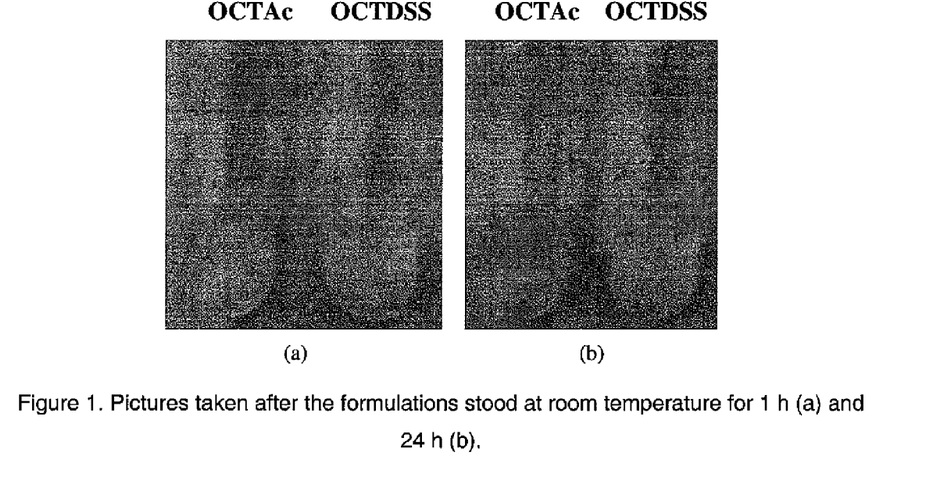
FIG. 1. shows the pictures taken after the formulations stood at room temperature for 1 h (a) and 24 h (b).

Although a higher concentration of SAIB (80% vs. 70% in Example 7) was used, when the OCT-Ac was combined with SAIB/NMP solution, phase separation occurred even faster than that observed in Example 7. A chunky aggregate was formed at the bottom of the formulation (FIG. 1(a)). This inhomogeneous formulation is clearly not suitable for injection to form a consistent depot system in situ for controlled release. When the OCT-SDS was combined with SAIB/NMP solution, a homogeneous milky suspension was obtained and suitable for injection. Even after 24 hours, no significant phase separation was observed in the suspension (Figure (b)) and could be readily administered via injection using a syringe.

Example 9

In Vitro Release of Octreotide from Various Formulations

Formulations were prepared by mixing octreotide acetate (OCT-Ac), octreotide dodecyl sulfate (OCT-SDS) and octreotide docusate (OCT-DSS) complex powders with SAIB solution in NMP (90% w/w). The octreotide content was about 6% in each formulation as shown in Table 4.

TABLE 4

Formulations containing octreotide

| Formulation | Peptides (mg) | SAIB/NMP (mg) | Peptide Content (%) |
|---|---|---|---|
| OCT-Ac/SAIB/NMP | 66.0 | 934.0 | 6% |
| OCT-SDS/SAIB/NMP | 88.6 | 911.4 | 6% |
| OCT-DSS/SAIB/NMP | 104.1 | 895.9 | 6% |

An aliquot of the suspension was used for the in vitro release. About 0.1 mL of each formulation containing octreotide was injected into 3 mL of releasing buffer (PBS 7.4, containing 0.1% sodium azide) in a 4 mL glass vial. The vials were incubated at 37° C. and sampled at various time points. At each time point, 2 mL of release medium was removed and replaced with 2 mL of fresh release medium. The collected samples were analyzed for peptide concentration and integrity by HPLC using an YMC-Pack ODS-120A column. Triplicate samples were used for each formulation.

Figure 2:
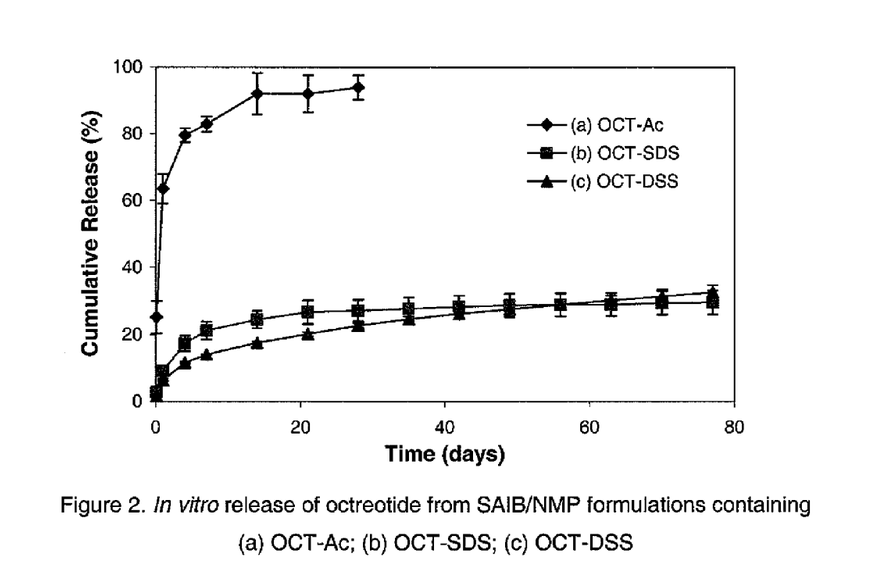
FIG. 2. shows the in vitro release of octreotide from SAIB/NMP formulations containing (a) OCT-Ac; (b) OCT-SDS; (c) OCT-DSS.

As shown in FIG. 2, the release of OCT from formulation containing OCT-Ac showed a very high initial burst release. More than 60% of the octreotide was released within 24 hours and more than 90% of the octreotide was released after two weeks. However, surprisingly, the release of OCT from formulations containing OCT-SDS and OCT-DSS did not show much initial burst release. Less than 10% of the octreotide was released within 24 hours from both formulations containing OCT-SDS and OCT-DSS followed by a gradual release over time.

Example 10

In Vitro Release of Leuprolide from Various Formulations

Formulations were prepared by mixing leuprolide acetate (LA-Ac), leuprolide dodecyl sulfate (LA-SDS), leuprolide docusate (LA-DSS) and leuprolide oleate (LA-OL) complex powders with SAIB solution in NMP (90% w/w). The leuprolide content was about 6% in each formulation as shown in Table 5.

TABLE 5

Formulations containing leuprolide

| Formulation | Peptides (mg) | SAIB/NMP (mg) | Peptide Content (%) |
|---|---|---|---|
| LA-Ac/SAIB/NMP | 67.1 | 932.9 | 6% |
| LA-SDS/SAIB/NMP | 93.9 | 906.1 | 6% |
| LA-DSS/SAIB/NMP | 112.4 | 887.6 | 6% |
| LA-OL/SAIB/NMP | 69.8 | 765.5 | 6% |

An aliquot of the suspension was used for the in vitro release. About 0.1 mL of each leuprolide formulation was injected into 3 mL of releasing buffer (PBS 7.4, containing 0.1% sodium azide) in a 4 mL glass vial. The vials were incubated at 37° C. and sampled at various time points. At each time point, 2 mL of release medium was removed and replaced with 2 mL of fresh release medium. The collected samples were analyzed for peptide concentration and integrity by HPLC using an YMC-Pack ODS-120A column. Triplicate samples were used for each formulation.

Figure 3:
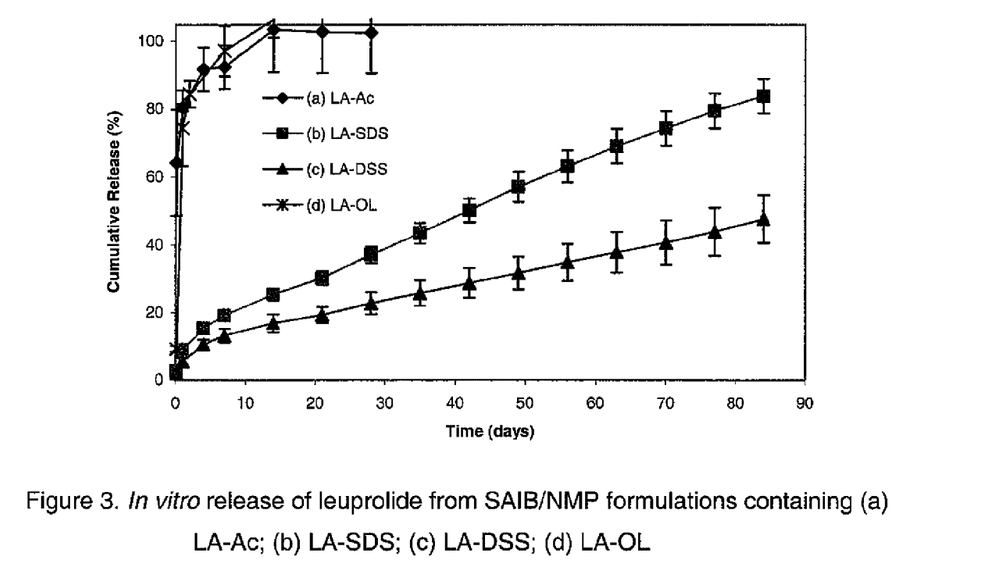
FIG. 3. shows the in vitro release of leuprolide from SAIB/NMP formulations containing (a) LA-Ac; (b) LA-SDS; (c) LA-DSS; (d) LA-OL.

As shown in FIG. 3, the release of leuprolide from formulations containing LA-Ac and LA-OL showed a very high initial burst release. More than 80% of the leuprolide was released within 24 hours and almost all of the leuprolide was released after two weeks. The complexation of leuprolide with oleate resulted in a water-insoluble complex, but it did not reduce the initial burst and overall release of leuprolide. However, surprisingly, the initial burst release of leuprolide from formulations containing LA-SDS and LA-DSS was dramatically reduced. Less than 10% of the leuprolide was released within 24 hours from both formulations containing LA-SDS and LA-DSS followed by a gradual zero order release over time.

Example 11

Preparation of Doxorubicin Docusate (DOX-DSS) and Dodecyl Sulfate (DOX-SDS)

1,4-Bis(2-ethyhexyl)sulfobutanedioate sodium (DSS, $C_{20}H_{37}NaO_7S$, MW: 444.56, 235.3 mg, 0.53 mmol) was dissolved in isopropanol (2 mL), and 200 mg (0.53 mmol) of doxorubicin hydrochloride (DOXHCl, $C_{27}H_{29}NO_{11}$.HCl, MW 579.98, >98.0%) was dissolved in water (20 mL). The DSS solution was mixed with the doxorubicin hydrochloride solution and stirred for one hour. The complex was separated by centrifugation at 3500 RPM, and the resulting precipitate was freeze-dried under vacuum.

Example 12

In Vitro Release of Doxorubicin from Various Formulations

Formulations were prepared using doxorubicin-HCl (DOX-HCl) and doxorubicin docusate (DOX-DSS) complex powders. Formulations were prepared by mixing DOX-HCL and DOX-DSS with SAIB solution in NMP to achieve 6% DOX loading as shown in Table 6.

TABLE 6

Formulations containing doxorubicin

| Formulation | DOX salts (mg) | SAIB (mg) | NMP (mg) | DOX Content (%) |
|---|---|---|---|---|
| DOX-HCl/SAIB/NMP | 63.3 | 707.1 | 286.1 | 6% |
| DOX-DSS/SAIB/NMP | 102.7 | 588.6 | 275.1 | 6% |

An aliquot of the suspension was used for studying the in vitro release of DOX from different formulations. About 0.1 mL of each DOX formulation was injected into 3 mL of releasing buffer (PBS 7.4, containing 0.1% sodium azide) in a 4 mL glass vial. The vials were incubated at 37° C. and sampled at various time points. At each time point, 2 mL of release medium was removed and replaced with 2 mL of fresh release medium. The collected samples were analyzed for peptide concentration and integrity by HPLC using an YMC-Pack ODS-120A column. Triplicate samples were used for each formulation.

As shown in Table 7, the release of DOX from formulation containing DOX-HCl showed a very high initial burst release. More than 70% of the DOX was released within 24 hours. However, surprisingly, the release of DOX from formulations containing DOX-DSS did not show much initial burst release. Less than 8% of the DOX was released within 24 hours from the formulation containing DOX-DSS. The results indicate that the complexation of DOX with DSS significantly reduces the initial burst release of DOX by almost 10 fold. The complexation will enable to deliver DOX over an extended period of time.

TABLE 7

Formulations containing doxorubicin

| | Release (%) | |
|---|---|---|
| Formulation | 3 h | 24 h |
| DOX-HCl/SAIB/NMP | 70.6 | 72.7 |
| DOX-DSS/SAIB/NMP | 0.5 | 7.3 |

Example 13

Preparation of the Complex of Pramipexole (PPL) with SDS (PPL-SDS)

80.7 mg of pramipexole (PPL, MW 302.27) was dissolved in 2 mL of DI water (0.267 mmol). 2.662 mL of SDS solution (MW 288.38, 57.83 mg/mL) was added in a 1:2 ratio (0.534 mmol) of PPL:SDS and the solution was mixed well. A white precipitate formed. The pH was adjusted from 4 to 7 with NaOH. The solution was frozen and placed on the freeze dryer overnight. A white powder was obtained.

Example 14

In Vitro Release of Pramipexole from SAIB Formulations

Formulations containing about 6% PPL of different salt forms were prepared by mixing PPL with 90% SAIB solutions in NMP. Injections of roughly 100 mg were made into vials with 3 mL PBS buffer and 0.1% $NaN_3$. Gel-like pellets formed and the vials were placed on a shaker at 37° C. The release of PPL was measured by removing 2 mL of the release media at specified times and replacing it with 2 mL of fresh buffer. The concentration in the release media was determined by reverse phase HPLC.

TABLE 6

Formulations containing doxorubicin

| Formulation | PPL salts (mg) | SAIB/NMP (90%) (mg) | PPL Content (%) |
|---|---|---|---|
| PPL-HCl/SAIB/NMP | 65.2 | 1018.8 | 6% |
| PPL-SDS/SAIB/NMP | 168.3 | 797.5 | 6% |

Figure 4:
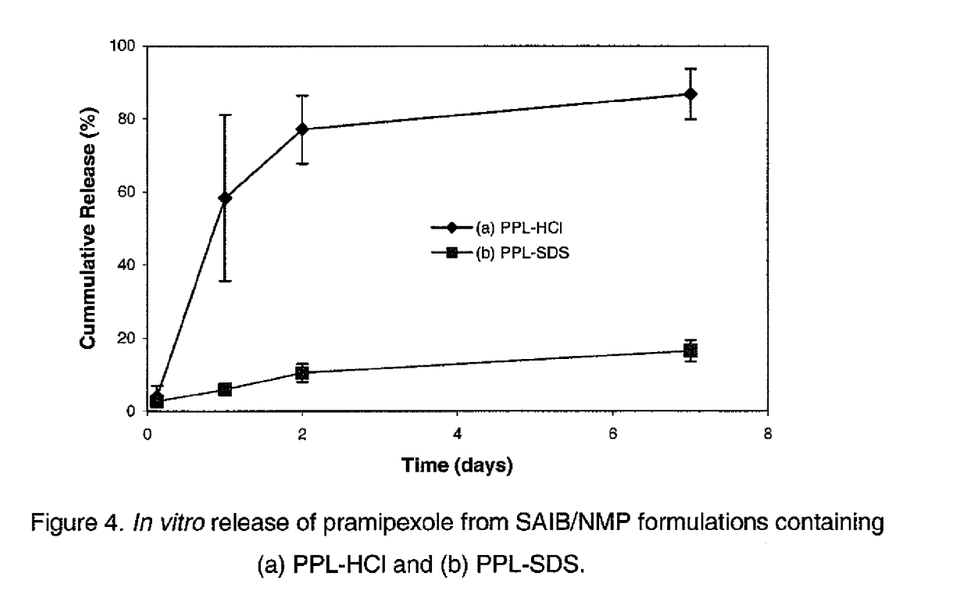
FIG. 4. shows the in vitro release of pramipexole from SAIB/NMP formulations containing (a) PPL-HCl and (b) PPL-SDS.

As shown in FIG. 4, the release of pramipexole from formulations containing PPL-HCl showed a very high initial burst release. More than 60% of the pramipexole was released within 24 hours and about 90% of the pramipexole was released after one week. However, surprisingly, the initial burst release of pramipexole from formulations containing PPL-SDS was dramatically reduced. Less than 5% of the pramipexole was released within 24 hours from both formulations containing PPL-SDS followed by a gradual near zero order release over time.

Example 15

Preparation of Gentamycin Docusate (GEN-DSS)

79.7 mg of gentamycin (2-[4,6-diamino-3-[3-amino-6-(1-methylaminoethyl)tetrahydropyran-2-yl]oxy-2-hydroxy-cyclohexoxy]-5-methyl-4-methylamino-tetrahydropyran-3,5-diol, MW 477.6 g/mol and 5 ionizable (charge) groups)

sulfate salt (GEN sulfate, MW 694-723, 88.2%) was dissolved in 2 mL of DI water (0.125 mmol). 4.877 mL of DSS solution (MW 444.55, 57.11 mg/mL) was added to achieve a 5:1 ratio of DSS:GEN. A white precipitate formed immediately upon addition of the DSS solution. The solution was frozen and placed in the freeze dryer overnight.

Example 16

Preparation of Formulation Containing GEN-DSS

Formulations containing about 6% and 2% GEN-DSS with 90% SAIB in NMP were prepared. Injections of roughly 100 mg were made into vials with 3 mL PBS buffer and 0.1% $NaN_3$. Gel-like pellets were formed at room temperature. However, after the vials were incubated at 37° C., the pellets began to disintegrate and fall apart within a few hours.

Example 17

Preparation of Lysozyme Docusate (LYZ-DSS)

50.5 mg of lysozyme (MW 18,000) was dissolved in 1 mL of DI water (0.0028 mmol). 148.2 μL of DSS solution (MW 444.55, 58.86 mg/mL) was added to achieve a 7:1 ratio of DSS:LYZ. A white precipitate formed immediately upon addition of the DSS solution. The solution was frozen and placed on the freeze dryer overnight.

Example 18

Preparation of Formulation Containing Lysozyme Docusate (LYZ-DSS)

Formulations containing about 6% LYZ and LYZ-DSS (85.2% LYZ) with 90% SAIB in NMP were prepared. Injections of roughly 100 mg were made into vials with 3 mL PBS buffer and 0.1% $NaN_3$. Gel-like pellets were formed at room temperature and put on a shaker at 37° C. The pellets containing LYZ phase separated after one day with the pellet having a white opaque center surrounded by a transparent layer. The pellets containing LYZ-DSS remained one phase as uniform white pellets. An improved depot system was achieved the complexation of lysozyme with amphiphilic molecule DSS.

Example 19

Preparation of Naltrexone Docusate (NT-DSS)

1,4-Bis(2-ethyhexyl)sulfobutanedioate sodium (DSS, $C_{20}H_{37}NaO_7S$, MW: 444.56, 235.3 mg, 0.53 mmol) was dissolved in isopropanol (2 mL), and 200 mg (0.53 mmol) of Naltrexone hydrochloride (NT, $C_{20}H_{23}NO_4$·HCl, MW 377.86, >99.0%) was dissolved in water (20 mL). The DSS solution was mixed with the Naltrexone hydrochloride solution and stirred for one hour. The complex was separated by centrifugation at 3500 RPM, and the resulting precipitate was freeze-dried under vacuum.

The invention is not limited by the embodiments described above which are presented merely as examples and can be modified in various ways within the scope of protection defined by the appended patent claims.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A liquid composition for sustained release of a bioactive substance, consisting essentially of:
   (a) sucrose acetate isobutyrate;
   (b) a solvent selected from the group consisting of acetone, benzyl alcohol, butylene glycol, caprolactam, caprolactone, dimethylsulfoxide, ethanol, ethyl acetate, ethyl lactate, glycerol, glycerol formal, glycofurol, tetraglycol, N-methyl-2-pyrrolidone, polyethylene glycol, methoxy polyethylene glycol, alkoxy polyethylene glycol, propylene carbonate, 2 pyrrolidone, triacetin and triethyl citrate; and
   (c) an ionic complex that is formed between a bioactive substance having a net charge at neutral pH in water and an amphiphilic molecule, wherein the amphiphilic molecule is selected from the group consisting of dialkyl ester sulfosuccinic acid, dioctyl sulfosuccinic acid, benzenesulfonic acid, camphorsulfonic acid, (+)-(1S)camphor-10-sulfonic acid, dodecylsulfuric acid, naphthalene-2-sulfonic acid, naphthalene-1,5-disulfonic acid, para-toluenesulfonic acid, cholesterol sulfuric acid and heptanesulfonic acid.

2. The composition of claim 1, wherein the bioactive substances are small molecules, macromolecules, peptides, proteins, or enzymes.

3. The composition of claim 1, wherein the molecular weight of the bioactive substance divided by the number of ionizable groups on the bioactive substance is greater than 100 daltons.

4. The composition of claim 1, wherein the bioactive substance is selected from the group consisting of 4-hydroxyphenethylamine, methylamphetamine, amitriptyline, reboxetine, bupropion, mirtazapine, venlafaxine, duloxetine, fluoxetine, paroxetine, escitalopram, citalopram, sertraline, bromocriptine, pergolide, pramipexole, ropinirole, cabergoline, apomorphine, lisuride, doxorubicin, doxycyclin, diltiazam, cyclobenzaprine, bacitracin, noscapine, erythromycin, polymyxin, vancomycin, nortriptyline, quinidine, ergotamine, benztropine, verapamil, flunarizine, imipramine, gentamycin, kanamycin, neomycin, amoxicillin, amikacin, arbekacin, bambermycins, butirosin, dibekacin, dihydrostreptomycin, fortimicin, isepamicin, micronimicin, netilmicin, paromycin, ribostamycin, rapamycin, sisomicin, streptomycin and tobramycin, streptomycin and tobramycin, pyrimethamine, naltrexone, lidocaine, prilocalne, mepivacaine, bupivacaine, tetracaine, ropivacaine, and resperidone.

5. The composition of claim 1, wherein the bioactive substance is selected from the group consisting of oxytocin, vasopressin, adrenocorticotropic hormone, epidermal growth factor, platelet-derived growth factor, prolactin, luteinising hormone, luteinizing hormone releasing hormone, luteinizing hormone releasing hormone agonists, luteinizing hormone releasing hormone antagonists, growth hormones, growth hormone releasing factor, insulin, erythropoietin, somatostatin, glucagon, interleukin, interferon-α, interferon-β, interferon-γ, gastrin, tetragastrin, pentagastrin, urogastrone, secretin, calcitonin, enkephalins, endorphins, angiotensins, thyrotropin releasing hormone, tumor necrosis factor, parathyroid hormone, nerve growth factor, granulocyte-colony stimulating factor, granulocyte macrophage-colony stimulating factor, macrophage-colony stimulating factor, heparinase, vascular endothelial growth factor, bone morphogenic protein, exenatide, renin, bradykinin, bacitracins, polymyxins, colistins, tyrocidine, gramicidins, cyclosporins, enzymes, cytokines, antibodies, vaccines, antibiotics, antibodies, glycoproteins, follicle stimulating hormone, kyotorphin, taftsin, thymopoietin, thymosin, thymostimulin, thymic humoral factor, serum thymic factor, colony stimulating factors, motilin, bombesin, dinorphin, neurotensin, cerulein, urokinase, kallikrein, angiotensin II, blood coagulation factor VII and IX, lysozyme, gramicidines, melanocyte stimulating hormone, thyroid hormone releasing hormone, thyroid stimulating hormone, pancreozymin, cholecystokinin, human placental lactogen, human chorionic gonadotrophin, protein synthesis stimulating peptide, gastric inhibitory peptide, vasoactive intestinal peptide, and platelet derived growth factor.

6. A liquid composition for sustained release of a bioactive substance, consisting essentially of:
(a) sucrose acetate isobutyrate;
(b) a solvent selected from the group consisting of acetone, benzyl alcohol, butylene glycol, caprolactam, caprolactone, dimethylsulfoxide, ethanol, ethyl acetate, ethyl lactate, glycerol, glycerol formal, glycofurol, tetraglycol, N-methyl-2-pyrrolidone, polyethylene glycol, methoxy polyethylene glycol, alkoxy polyethylene glycol, propylene carbonate, 2 pyrrolidone, triacetin and triethyl citrate;
(c) an ionic complex that is formed between a bioactive substance having a net charge at neutral pH in water and an amphiphilic molecule, wherein the amphiphilic molecule is selected from the group consisting of dialkyl ester sulfosuccinic acid, dioctyl sulfosuccinic acid, benzenesulfonic acid, camphorsulfonic acid, (+)-(1S)camphor-10-sulfonic acid, dodecylsulfuric acid, naphthalene-2-sulfonic acid, naphthalene-1,5-disulfonic acid, para-toluenesulfonic acid, cholesterol sulfuric acid and heptanesulfonic acid; and
(d) an additive selected from the group consisting of polylactides, polyglycolides, polycaprolactones, polyanhydrides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, chitin, chitosan, and hyaluronic acid.

7. A liquid composition for sustained release of a bioactive substance, consisting essentially of:
(a) sucrose acetate isobutyrate;
(b) a solvent selected from the group consisting of acetone, benzyl alcohol, butylene glycol, caprolactam, caprolactone, dimethylsulfoxide, ethanol, ethyl acetate, ethyl lactate, glycerol, glycerol formal, glycofurol, tetraglycol, N-methyl-2-pyrrolidone, polyethylene glycol, methoxy polyethylene glycol, alkoxy polyethylene glycol, propylene carbonate, 2 pyrrolidone, triacetin and triethyl citrate;
(c) an ionic complex that is formed between a bioactive substance having a net charge at neutral pH in water and an amphiphilic molecule, wherein the amphiphilic molecule is selected from the group consisting of dialkyl ester sulfosuccinic acid, dioctyl sulfosuccinic acid, benzenesulfonic acid, camphorsulfonic acid, (+)-(1S)camphor-10-sulfonic acid, dodecylsulfuric acid, naphthalene-2-sulfonic acid, naphthalene-1,5-disulfonic acid, para-toluenesulfonic acid, cholesterol sulfuric acid and heptanesulfonic acid; and
(d) an additive selected from the group consisting of cysteine, methionine, d-alpha tocopherol acetate, dl-alpha tocopherol, ascorbyl palmitate, butylated hydroxyanidole, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutyrophenone, dimethylphenol, ditertbutylphenol, vitamin E, and lecithin.

8. The composition of claim 1, wherein the bioactive substance is selected from the group consisting of doxorubicin, pramipexole, octreotide, and leuprolide.

9. The composition of claim 1, wherein the amphiphilic molecule is selected from the group consisting of dioctyl sulfosuccinic acid and dodecylsulfuric acid.

10. The composition of claim 1, wherein the ratio of sucrose acetate isobutyrate to solvent is from 50:50 to 95:5.

11. The composition of claim 1, wherein the ratio of sucrose acetate isobutyrate to solvent is from 70:30 to 90:10.

* * * * *